(12) United States Patent
Baumgartner et al.

(10) Patent No.: US 9,795,794 B2
(45) Date of Patent: Oct. 24, 2017

(54) PULSE WIDTH ADAPTATION FOR INDUCTIVE LINKS

(75) Inventors: Josef Baumgartner, Ranggen (AT); Jose Rodriguez-Navarro, Serfaus (AT); Martin Stoffaneller, Innsbruck (AT); Andreas Mitterer, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 1163 days.

(21) Appl. No.: 12/182,255

(22) Filed: Jul. 30, 2008

(65) Prior Publication Data

US 2009/0043361 A1 Feb. 12, 2009

Related U.S. Application Data

(60) Provisional application No. 60/955,063, filed on Aug. 10, 2007.

(51) Int. Cl.
*A61N 1/372* (2006.01)

(52) U.S. Cl.
CPC .......... *A61N 1/37211* (2013.01); *A61N 1/372* (2013.01); *A61N 1/3727* (2013.01); *A61N 1/37223* (2013.01)

(58) Field of Classification Search
USPC .............................. 607/57, 32, 27
See application file for complete search history.

(56) References Cited

U.S. PATENT DOCUMENTS

| | | | |
|---|---|---|---|
| 4,233,684 A | 11/1980 | Eggermont | 375/30 |
| 4,284,856 A | 8/1981 | Hochmair et al. | 179/107 |
| 4,357,497 A | 11/1982 | Hochmair et al. | 179/107 |
| 4,428,377 A | 1/1984 | Zollner et al. | 128/419 R |
| 4,592,359 A | 6/1986 | Galbraith | 128/419 R |
| 4,612,654 A | 9/1986 | DeFreitas | 375/30 |
| 5,027,306 A | 6/1991 | Dattorro et al. | 364/724 |
| 5,069,210 A | 12/1991 | Jeutter et al. | 128/420.6 |
| 5,144,306 A | 9/1992 | Masuda | 341/76 |
| 5,215,085 A | 6/1993 | von Wallenberg-Pachaly | 128/420.6 |
| 5,305,004 A | 4/1994 | Fattaruso | 341/120 |
| 5,408,235 A | 4/1995 | Doyle et al. | 341/143 |
| 5,549,658 A | 8/1996 | Shannon et al. | 607/57 |

(Continued)

FOREIGN PATENT DOCUMENTS

| | | | |
|---|---|---|---|
| EP | 1124211 A2 | 8/2001 | G08C 17/02 |
| WO | WO 99/49815 | 10/1999 | A61F 2/18 |

OTHER PUBLICATIONS

Chakravarthy, C. V., "An amplitude-controlled adaptive delta sigma modulator", *The Radio and Electronic Engineer*, vol. 49, No. 1, pp. 49-54, Jan. 1979.

(Continued)

*Primary Examiner* — Carl H Layno
*Assistant Examiner* — Jon Eric C Morales
(74) *Attorney, Agent, or Firm* — Sunstein Kann Murphy & Timbers LLP

(57) ABSTRACT

A signal processor is described for communication with an implanted medical device. An external processor transmits to the implanted medical device an implant data signal having a sequence of HI and LOW logic states at a fixed data bit rate. The pulse width durations of the HI and LOW logic states is adjustable in response to feedback telemetry data from the implantable medical device.

5 Claims, 5 Drawing Sheets

(56) References Cited

U.S. PATENT DOCUMENTS

| | | | |
|---|---|---|---|
| 5,571,148 A | 11/1996 | Loeb et al. | 607/56 |
| 5,601,617 A | 2/1997 | Loeb et al. | 607/56 |
| 5,609,616 A | 3/1997 | Schulman et al. | 607/56 |
| 5,626,629 A | 5/1997 | Faltys et al. | 607/57 |
| 5,721,783 A | 2/1998 | Anderson | 381/68.6 |
| 5,733,313 A | 3/1998 | Barreras, Sr. et al. | 607/33 |
| 5,741,314 A | 4/1998 | Daly et al. | 607/60 |
| 5,749,912 A | 5/1998 | Zhang et al. | 607/57 |
| 5,824,022 A | 10/1998 | Zilberman et al. | 607/57 |
| 5,938,691 A | 8/1999 | Schulman et al. | 607/57 |
| 5,957,958 A | 9/1999 | Schulman et al. | 607/57 |
| 6,002,966 A | 12/1999 | Loeb et al. | 607/57 |
| 6,026,125 A | 2/2000 | Larrick, Jr. et al. | 375/295 |
| 6,031,862 A | 2/2000 | Fullerton et al. | 375/200 |
| 6,067,474 A | 5/2000 | Schulman et al. | 607/57 |
| 6,073,050 A * | 6/2000 | Griffith | 607/57 |
| 6,167,310 A * | 12/2000 | Grevious | 607/32 |
| 6,175,767 B1 | 1/2001 | Doyle, Sr. | 607/57 |
| 6,181,969 B1 | 1/2001 | Gord | 607/59 |
| 6,219,580 B1 | 4/2001 | Faltys et al. | 607/57 |
| 6,289,247 B1 | 9/2001 | Faltys et al. | 607/57 |
| 6,295,472 B1 | 9/2001 | Rubinstein et al. | 607/55 |
| 6,308,101 B1 | 10/2001 | Faltys et al. | 607/57 |
| 6,535,153 B1 | 3/2003 | Zierhofer | 341/143 |
| 6,594,525 B1 | 7/2003 | Zierhofer | 607/57 |
| 6,600,955 B1 | 7/2003 | Zierhofer | 607/57 |
| 6,661,363 B2 | 12/2003 | Zierhofer | 341/143 |
| 6,727,833 B2 | 4/2004 | Zierhofer | 341/143 |
| 6,778,858 B1 | 8/2004 | Peeters | 607/57 |
| 6,810,289 B1 | 10/2004 | Shaquer | 607/57 |
| 6,826,430 B2 | 11/2004 | Faltys et al. | 607/137 |
| 7,209,523 B1 | 4/2007 | Larrick et al. | 375/295 |
| 2001/0031909 A1 | 10/2001 | Faltys et al. | |
| 2004/0039423 A1* | 2/2004 | Dolgin | 607/27 |
| 2005/0077872 A1 | 4/2005 | Single | |
| 2005/0107843 A1 | 5/2005 | McDermott et al. | |
| 2005/0203589 A1 | 9/2005 | Zierhofer | |
| 2006/0052841 A1 | 3/2006 | Daly et al. | |
| 2006/0265061 A1 | 11/2006 | Kwon et al. | |

OTHER PUBLICATIONS

Galbraith, D, et al, "A Wide-Bank Efficient Inductive Transdermal Power and Data Link with Coupling Insensitive Gain", *IEEE Transactions on Biomedical Engineering*, vol. BME-34, No. 4, pp. 265-275, Apr. 1987.

Gheewala, T, et al, "A CMOS Implantable Multielectrode Auditory Stimulator for the Deaf", *IEEE Journal of Solid-State Circuits*, pp. 472-479, Dec. 1975.

Wilson, B.S., et al, "Comparative Studies of Speech Processing Strategies for Cochlear Implants", *Laryngoscope*, vol. 96, No. 10, pp. 1068-1077, Oct. 1988.

Wilson, B. S., et al, "Better speech recognition with cochlear implants", *Nature*, vol. 352, pp. 236-238, Jul. 18, 1991.

Wilson, B. S., et al, "Seventh Quarterly Progress Report; Speech Processors for Auditory Prostheses", *Center for Auditory Prosthesis Research*, pp. 1-69, 1994.

Zierhofer, C. M., et al, "Geometric Approach for Coupling Enhancement of Magnetically Coupled Coils", *IEEE Transactions on Biomedical Engineering*, vol. 43, No. 7, pp. 708-714, Jul. 1996.

Zierhofer, C. M., "Adaptive Sigma-Delta Modulation with One-Bit Quantization", *IEEE Transactions on Circuits and Systems-II: Analog and Digital Signal Processing*, vol. 47, No. 5, pp. 408-415, May 2000.

Zierhofer, C. M., et al, "Electronic Design of a Cochlear Implant for Multichannel High-Rate Pulsatile Stimulation Strategies", *IEEE Transactions on Rehabilitation Engineering*, vol. 3, No. 1, pp. 112-116, Mar. 1995.

Zierhofer, C. M., et al "High-Efficiency Coupling-Insensitive Transcutaneous Power and Data Transmission Via an Inductive Link", *IEEE Transactions on Biomedical Engineering*, vol. 37, No. 7, pp. 716-722, Jul. 1990.

European Patent and Trademark Office, International Search Report and Written Opinion, PCT/US2008/701520, dated Oct. 7, 2008.

\* cited by examiner

PULSE WIDTH ADAPTATION FOR INDUCTIVE LINKS

This application claims priority from U.S. Provisional Patent Application 60/955,063, filed Aug. 10, 2007, which is incorporated herein by reference.

FIELD OF THE INVENTION

The present invention relates to digital data and energy transmission methods for use with implantable medical devices, and more specifically, to signal conditioning of the data signal to be more robust against random variations and unknown parameters.

BACKGROUND ART

Many implantable medical devices receive an externally generated data signal which may also act as the source of electrical power for the implant. Typically, data signals are transferred in such systems using Near Field Communication (NFC) in the high-frequency (HF) radio frequency (RF) band (3-30 MHz) over an electromagnetic field induction link. For example, a magnetic field induction (MFI) link can transmit and receive data between an external signal processor and the implanted device based on transformer-type induction between two aligned coils—one external and one internal.

The external signal processor in such applications can be thought of as a self powered initiator (e.g., by batteries), where the implanted device is a non-self powered target device that is remotely powered through the MFI link by extracting electrical energy from the transmitted RF data signal. The implanted device can answer to an external command to provide telemetry feedback data, for example, by load modulation of the transmitted signal by the implanted device. A telemetry circuit in the external signal processor then can demodulate this load-modulated RF feedback signal.

Digital data transmission generally occurs at a fixed data bit rate of some R bits/second. FIG. 1 shows the simple case of data bits as logic ONEs and ZEROs (possibly encoded) which are transmitted from the initiator device to the target device using on-off keying (OOK) modulation (which is a special case of amplitude shift-keying (ASK)). As seen in the bottom of FIG. 1, the RF carrier signal is a sinusoid wave with a fundamental frequency ($f_c$) typically in the HF band. Data bit rates are typically less than or equal to $f_c/10$ bits per second. Under low power constraints, a non-linear power amplifier (PA) such as a Class E amplifier modulates and amplifies the baseband signal at the initiator device producing the waveform shown at the bottom of FIG. 1. Demodulation and detection of the modulated OOK signal takes place at the target device to produce the signal shown at the top of FIG. 1.

Under low-complexity constraints, demodulation and detection make use of non-coherent schemes. That is, in contrast to coherent schemes based on phase-locked loops (PLLs) and Costas loops which are relatively complex to implement, in non-coherent approaches demodulation is performed without recovering the rf carrier and detection is performed without recovering the original timing. In the example shown in FIG. 1, the baseband signal is Manchester encoded so that a positive (negative) transition signifies a logic ONE (ZERO), and there is a signal transition at mid-bit. Note that independent of the bit stream and inherent to Manchester encodings, only two states are visible: either a double-wide HI (double-wide LO) or a single-wide HI (single-wide LO).

Low-complexity detection methods are commonly used which are based on asynchronous over-sampling and counting (O&C) algorithms, but these are not very robust against variations. In asynchronous over-sampling, the demodulated signal is sampled at some kR samples per second (k is usually a number greater than 3) by a clock unrelated to the encoder clock (no frequency or phase relationship between the clocks is imposed). The counting algorithm counts the samples in a HI (LO) state and decides based on a fixed decision interval (i.e. a discrete set of integers) whether the current count signifies a double-wide HI (double-wide LO) or a single-wide HI (single-wide LO). Decoding into a logic ONE/ZERO stream (i.e. a non-return to zero stream, NRZ stream) follows straightforwardly. Data detection is discussed at greater length in the following: U.S. Pat. Nos. 5,741,314; 6,600,955; 4,361,895; and U.S. Pat. No. 6,628,212; the contents of which are incorporated herein by reference.

SUMMARY OF THE INVENTION

Embodiments of the present invention are directed to a signal processor for communication with an implanted medical device. An external processor transmits to the implanted medical device an implant data signal having a sequence of HI and LOW logic states at a fixed data bit rate. The pulse width durations of the HI and LOW logic states is adjustable in response to feedback telemetry data from the implantable medical device.

In specific embodiments, the external processor may use an electromagnetic field induction link for transmitting a high-frequency band radio frequency between 3 MHz and 30 MHz. The implant data signal may be encoded using Manchester data encoding. The adjustable pulse width durations may be selectable from a group of pre-determined pulse width durations.

In any of the above embodiments, the implanted medical device may be a cochlear implant device.

DETAILED DESCRIPTION OF SPECIFIC EMBODIMENTS

For a near field communication (NFC) system as implemented for an implantable device such as a cochlear implant, variations in parameters and conditions strongly affect the shape of the HF signal and therefrom the duration of HI and LO logic states. Therefore, the robustness of a detection algorithm based on an O&C algorithm is strongly limited by the over-sampling factor (k) and the decision intervals. While k strongly affects power consumption (the higher k, the higher power consumption) and is therefore limited, the decision intervals are a free design parameter. In order to improve robustness, the decision intervals may be defined in an adaptive manner where a known training sequence at startup sets the optimum interval at the target's decoder.

As explained above, a typical NFC system may be characterized by:
 passive NFC,
 an initiator,
 an inductive link,
 OOK modulation of a RF sinusoid (forward link),
 non-coherent demodulation and detection, and
 load modulation at the target (back telemetry link).

Under these constraints, if the separation between the coils (D) and their misalignment is a priori unknown (within some known interval), then the problem of implementing a robust detection algorithm becomes difficult: the bandwidth (B) and the quality factor (Q) of the HF link vary with D, and therefore the shape of the transmitted HF signal also varies with D (amplitude variations). A high Q, and therefore low B, limits the transition time of the HF signal and leads to signal degradation (causing inter symbol interference). If, additionally, variations due to electronic components, that is, discrete components, or process variations in integrated circuits (IC) are taken into account, then the detection problem gets harder. NFC systems of this class include, among others, data transmission systems in medical implants (e.g. cochlear implants), contact-less smartcards, and, in general, RFID systems.

Figure 1:
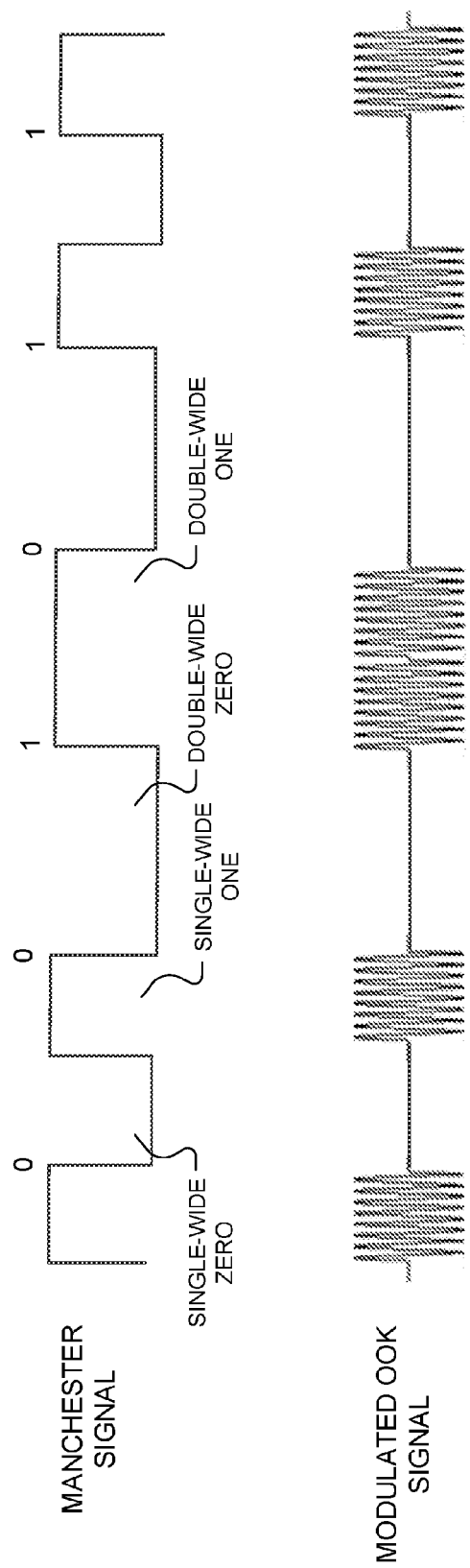
FIG. 1 shows data transmission in an NFC system as described herein.
Figure 2:
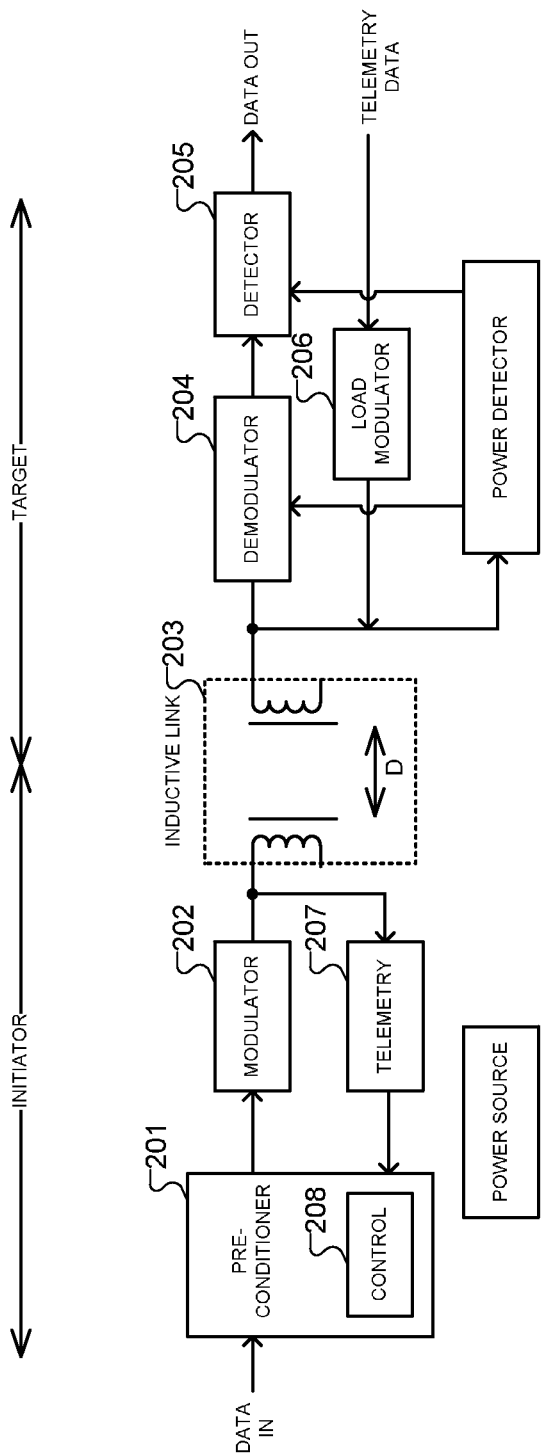
FIG. 2 shows various functional blocks in a system according to a specific embodiment of the present invention.

FIG. 2 illustrates various functional blocks in one specific embodiment of the present invention. An external processor device includes a signal pre-conditioner 201 which sets an optimal pulse width of the initiator baseband signal at start-up. Modulator 202 then encodes the pre-conditioned baseband signal (Manchester encoded) using OOK modulation and the data signal is transmitted to the target device by an inductive link 203. Within the target device, the received modulated OOK signal is processed by demodulator 204 and detector 205. Telemetry feedback data is encoded by load modulator 206 and detected in the initiator device by telemetry circuit 207 for use by the control block 208 within the pre-conditioner 201.

Figure 3:
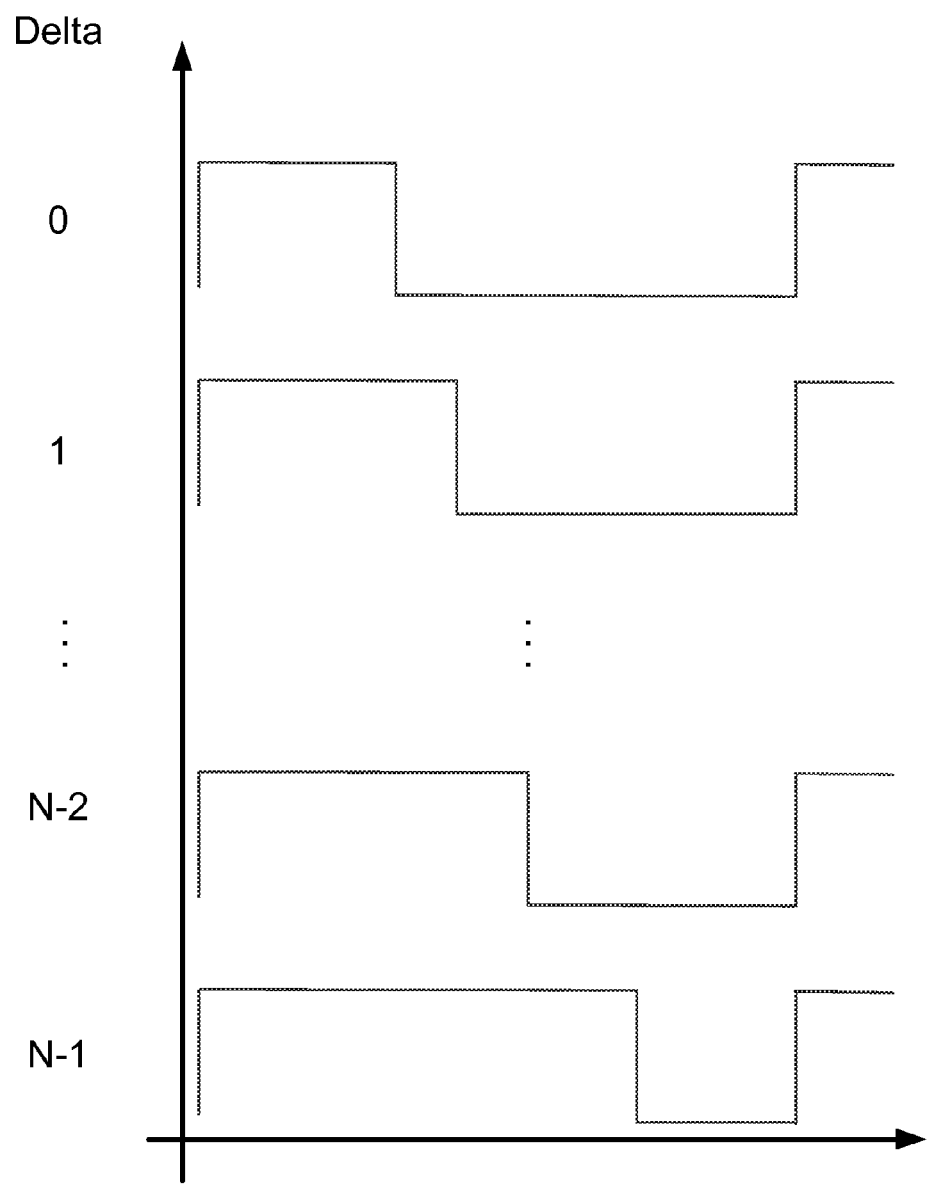
FIG. 3 illustrates pulse width adaptation using various waveform deltas according to a specific embodiment.

In the pre-conditioner 201, the pulse width ratio between the HI logic state and LO logic state, referred to as the "delta" is set as shown in FIG. 3. Note that the bit duration of the Manchester signal remains the same. The delta is selected from a finite set by the control block 208. The delta directly affects the shape of the transmitted RF signal sent over the inductive link 203, and therefore the decision intervals can remain fixed.

Figure 4:
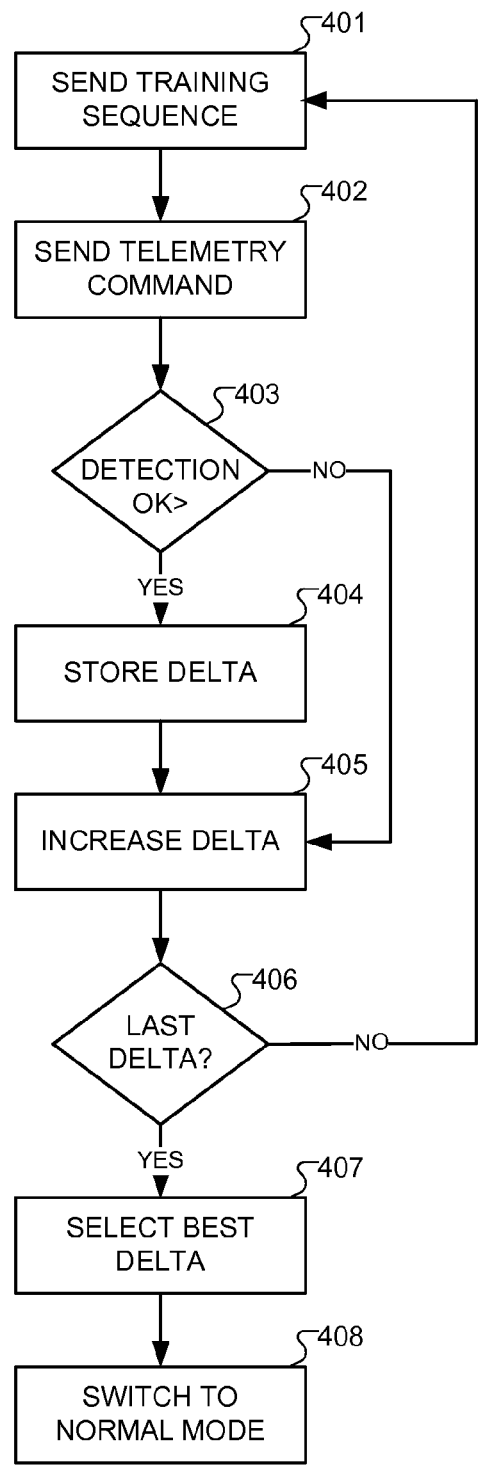
FIG. 4 illustrates various steps in optimizing the waveform delta according to a specific embodiment.

A state machine in the control block 208 implements the specific procedure for setting the PW delta as shown in FIG. 4. After system power-up, the control block 208 selects the first delta and sends a test sequence, step 401. This training sequence may set one or more parameters of the target. Then, the control block 208 sends a telemetry command to the target, step 402, in order to read the previously set parameter based on the back telemetry signal sent by the target load modulator 206. In step 403, if the received parameter is not the correct one, then it is assumed that detection at the target failed (it is also assumed that the telemetry channel is a robust one which is usually the case). otherwise, detection worked correctly and this delta can be stored, step 405 and the test sequence delta is increased, step 405. This process is repeated, step 406, each one of the deltas in the test sequence. From all the stored deltas, one is selected as the "best," (perhaps arbitrarily, e.g., the delta in the middle of the longest interval). This completes the delta setting process, the system switches to normal mode of operation, step 408.

Figure 5:
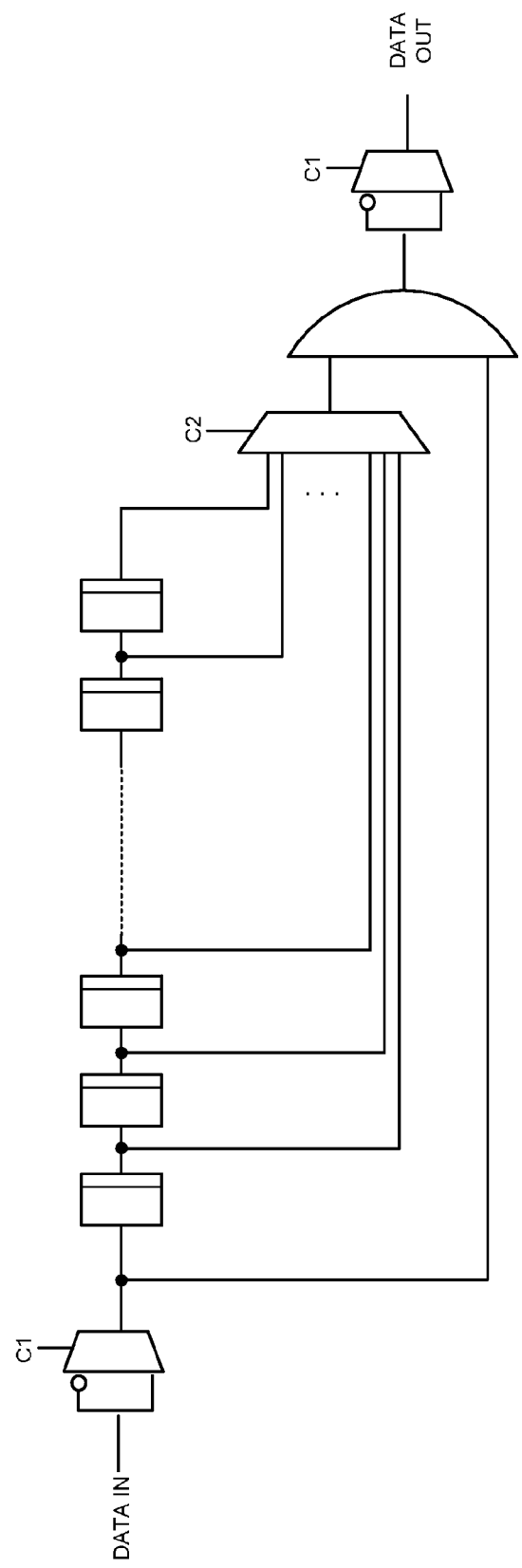
FIG. 5 illustrates one example of circuit logic for producing various waveform deltas in a specific embodiment.

FIG. 5 shows one example of a possible implementation of the pre-conditioning block 201 which sets the delta. Therein, bit signals C1 and C2 defined the current delta. DATA IN is given by the Manchester signal and DATA OUT is the signal already conditioned. DATA IN or its inverted version is selected thru the multiplexer by C1. This signal is stored in a shift register. The shift-register outputs are selected through a multiplexer by C2. The selected signal is ORed with the original signal or its inverted version. The output of the OR gate is again multiplexed by C1.

Embodiments of the invention may be implemented in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements (e.g., ASIC or FPGA), other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:
1. A method for communication with an implanted medical device, the method comprising:
 for implant data signals having sequences of HI and LOW logic states at a fixed data bit rate with adjustable pulse width durations, defining a group of pre-determined pulse width durations based on a pulse width setting process that includes:

i. transmitting to the implanted medical device a plurality of test sequence data signals using different pulse width durations, wherein each test sequence data signal sets one or more parameters of the implanted medical device, ii. for each of the test sequence data signals,
   (1) measuring a corresponding back telemetry signal from the implanted medical device communicating the one or more parameters set in the implanted medical device, and
   (2) comparing the one or more parameters set by the test sequence data signal to the one or more parameters communicated in the corresponding back telemetry signal, and iii. including the pulse width duration of a given test sequence data signal in the group of pre-determined pulse width durations when the one or more parameters set by each test sequence data signal correctly matches the one or more parameters communicated in the corresponding back telemetry signal; and operating the implanted medical device by transmitting the implant data signals with pulse width durations selected from the group of pre-determined pulse width durations.

2. A method according to claim 1, wherein the implant data signals are transmitted using an electromagnetic field induction link.

3. A method according to claim 1, wherein the implant data signals are transmitted using a high-frequency band radio frequency between 3 MHz and 30 MHz.

4. A method according to claim 1, wherein the implant data signal uses Manchester data encoding.

5. A method according to claim 1, wherein the implanted medical device is a cochlear implant device.

* * * * *